United States Patent
Elnajjar

(10) Patent No.: US 9,883,928 B2
(45) Date of Patent: Feb. 6, 2018

(54) DENTAL ARTICULATOR

(71) Applicant: Jean J. Elnajjar, Miami, FL (US)

(72) Inventor: Jean J. Elnajjar, Miami, FL (US)

(*) Notice: Subject to any disclaimer, the term of this patent is extended or adjusted under 35 U.S.C. 154(b) by 648 days.

(21) Appl. No.: 13/768,928

(22) Filed: Feb. 15, 2013

(65) Prior Publication Data

US 2014/0234797 A1 Aug. 21, 2014

(51) Int. Cl.
*A61C 11/00* (2006.01)
*A61C 11/08* (2006.01)

(52) U.S. Cl.
CPC .................. *A61C 11/08* (2013.01)

(58) Field of Classification Search
CPC ...................................... A61C 11/08
USPC ............................. 433/60; 285/9.1
See application file for complete search history.

(56) References Cited

U.S. PATENT DOCUMENTS

| | | | |
|---|---|---|---|
| 3,510,947 A | 5/1970 | Tuccillo et al. | |
| 4,319,875 A | 3/1982 | Beckwith | |
| 4,494,934 A | 1/1985 | Huffman | |
| 4,496,320 A | 1/1985 | Hwang et al. | |
| 4,522,591 A | 6/1985 | Braun et al. | |
| 4,533,323 A | 8/1985 | Huffman | |
| 4,548,581 A | 10/1985 | Huffman | |
| 4,734,033 A | 3/1988 | Huffman | |
| 4,797,097 A | 1/1989 | Cohn | |
| 4,842,242 A | 6/1989 | Huffman | |
| 5,007,829 A | 4/1991 | Farrell | |
| 5,044,949 A | 9/1991 | Xanthopoulos | |
| 5,221,203 A | 6/1993 | Callne | |
| 5,360,337 A | 11/1994 | Westdyk | |
| 5,425,636 A | 6/1995 | Ghim | |
| 5,605,456 A | 2/1997 | Young | |
| 5,622,497 A | 4/1997 | Cho | |
| 5,645,425 A | 7/1997 | Callne | |
| 5,769,634 A | 6/1998 | Choi | |
| 5,996,963 A | 12/1999 | Michael | |
| 6,163,911 A * | 12/2000 | Lin .......................... | B25B 9/00 7/165 |
| 6,382,969 B1 | 5/2002 | Elnajjar | |
| 6,450,809 B1 * | 9/2002 | Iverson .................. | A61C 11/02 433/57 |
| 6,508,646 B2 | 1/2003 | Pacino, Jr. et al. | |
| 7,112,061 B2 | 9/2006 | Callne | |
| 2008/0050694 A1 * | 2/2008 | Elnajjar ................. | A61C 11/00 433/64 |

* cited by examiner

Primary Examiner — Cris L Rodriguez
Assistant Examiner — Mirayda A Aponte
(74) Attorney, Agent, or Firm — Malloy & Malloy, P.L.

(57) ABSTRACT

A dental articulator apparatus and method of forming dental casts utilizing a dental articulator having pivotally connected upper and lower arms that each have a ball socket which receives a ball at the outer end of a respective model anchor, the opposed end of which is cast into a dental model. The model anchor ball is adjustably secured in the ball socket of the articulator arms by a set screw coupled with a rotatable magnetic extension rod that are installed, removed, advanced, and retracted as a unit and allow relative rotation between the set screw and the extension rod to facilitate fitting and positioning the ball in the socket when the set screw is loosened, and eliminate manually installing and positioning separate small shims and plungers that can be accidentally dropped and lost.

7 Claims, 4 Drawing Sheets

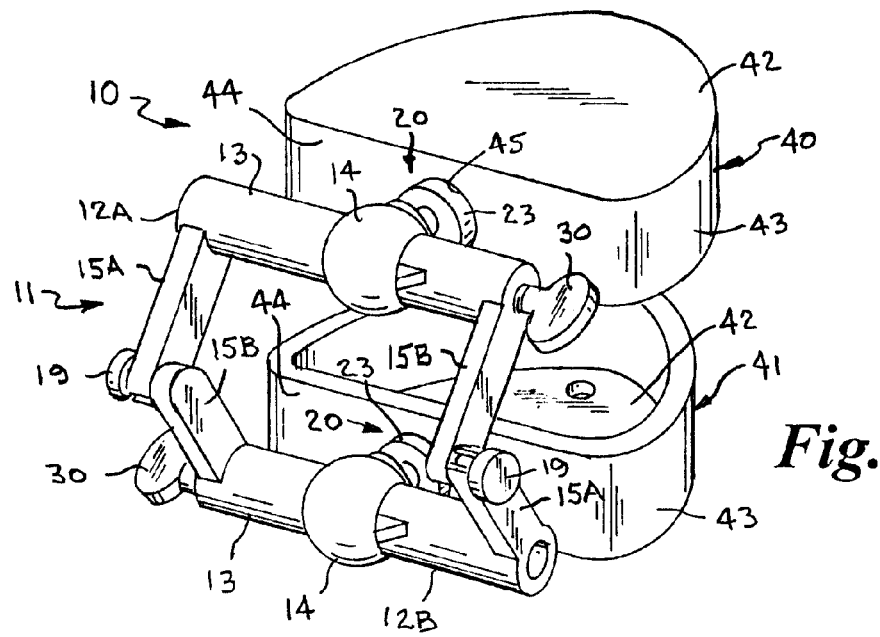
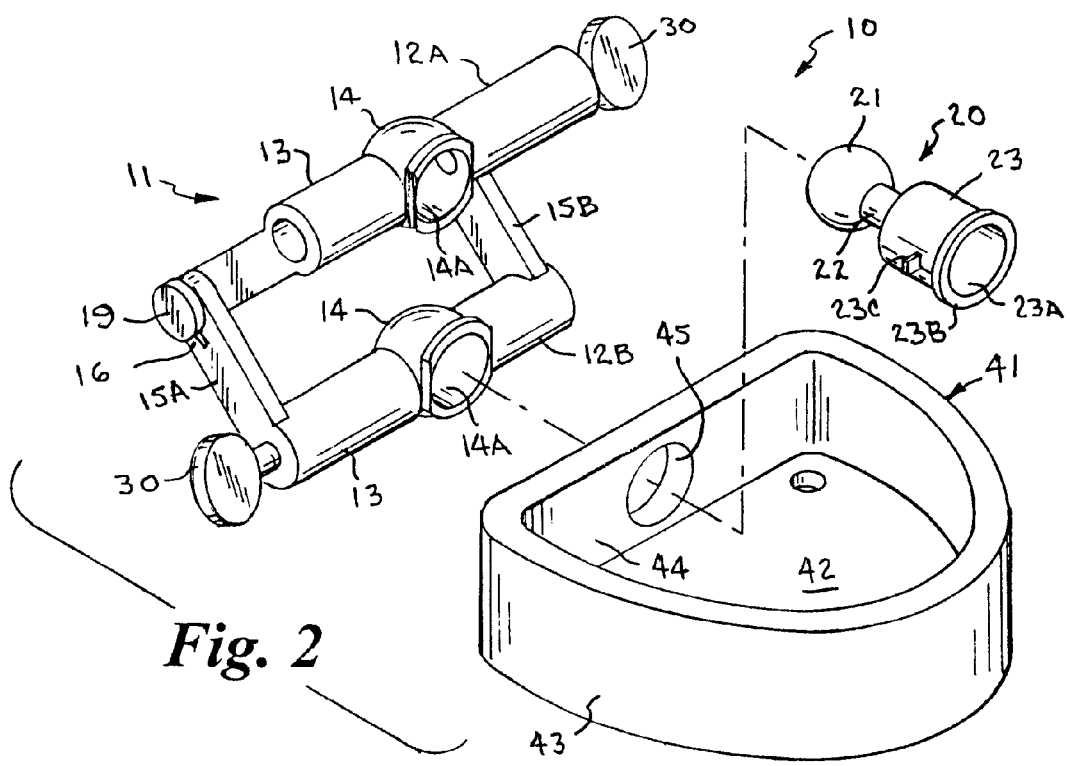
Fig. 1
Fig. 2

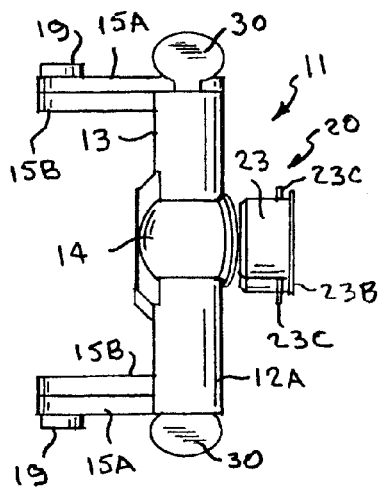
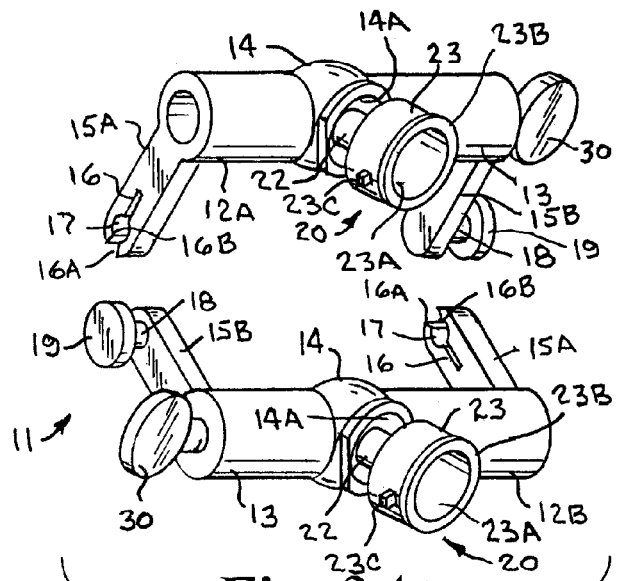
*Fig. 3D*   *Fig. 3A*
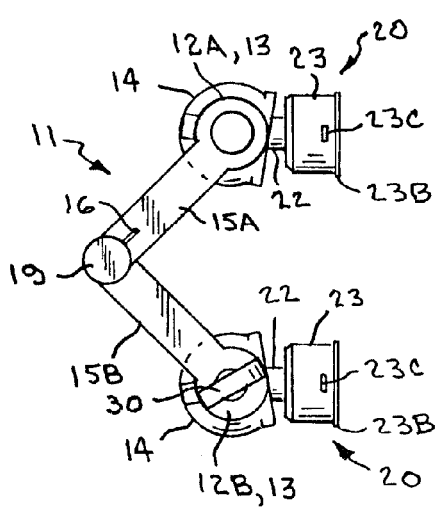
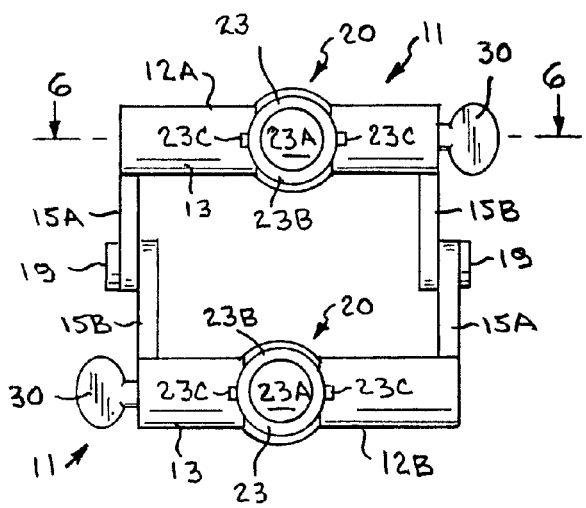
*Fig. 3C*   *Fig. 3B*

DENTAL ARTICULATOR

BACKGROUND OF THE INVENTION

1. Field of the Invention

The present invention relates generally to a device and method for a dental articulator for use with dental model casts, and, more specifically, to a dental articulator that is easily adjustable by the dental laboratory technician and/or dentist to align, as desired, the upper and lower dental model casts.

2. Background Art

Dental articulators, which hold and align together positive dental impressions, are well known in the prior art. Articulators are used to align the upper (maxilla) dental model with the lower (mandible) dental model, to simulate current or desired occlusion. By recreating the teeth and their occlusion (alignment) in model form, false teeth, caps and other dental prosthetics can be made in the precise size and shape necessary for the patient's mouth.

To create the dental models (casts), the dentist makes a negative impression of the patient's teeth. This impression may be a full mold (bilateral) or a partial quadrant mold (unilateral). The impression is obtained by filling a tray with thermoplastic material, and holding it against the patient's teeth and gums. After the thermoplastic material partially hardens (sets up), the tray is removed, leaving the negative impression of the teeth.

To form a positive impression of the teeth and their position, pourable hardenable stone, often called yellow stone, is poured into the negative impression. The positive impression is allowed to harden, and is then removed from the negative impression, forming a precise positive model of the teeth and their placement. The hard positive impression is then pressed into a forming mold containing new yellow stone. Forming molds, also known as "molds", "model formers", or "cast formers" are typically made of rubber or silicone, and are used to make the dental models. The yellow stone in the forming mold is in a flowable state and forms the base of the dental cast. The positive impression bonds with the new yellow stone base, excess yellow stone is scraped away, remaining yellow stone is allowed to harden, and the complete cast or dental model is now formed. This cast or dental model is then removed from the forming mold. The casts or models (upper and lower) are then attached to a dental articulator, which emulates the patient's jaw for aligning the upper and lower teeth/casts.

The prior art describes various devices and methods for fashioning and securing the dental cast base to the positive impression. Prior art also describes various devices and methods for securing the dental casts to a dental articulator.

Representative of the early prior art for dental cast bases are devices described in Tuccillo et al, U.S. Pat. No. 3,510, 947, and Beckwith, U.S. Pat. No. 4,319,875. These patents utilize bases having female plastic snap receivers. The positive impressions are fabricated with male studs, which snap into the female snap receivers of the base. This requires precise alignment of each male stud to properly mate with the female receiver. Repeated use wears down the male stud, causing loose snapping with the female receiver, thus making the alignment loose.

An alternative base system is described in Cho, U.S. Pat. No. 5,622,497, wherein a plastic base is adhered to a positive impression with a layer of stone material. The plastic base has a slot in which a disk is inserted and secured with a setscrew. The disk is attached to a stem having a ball at the other end, which connects to a reusable articulator. This system requires plastic bases that are relatively expensive, as is the non-disposable dental articulator.

The most common type of base system, however, is the type utilized in a series of patents issued to Huffman (U.S. Pat. Nos. 4,533,323; 5,548,581; 4,734,033; and 4,842,242). These patents and several others utilize base forming molds. Soft stone material is placed into a (typically) rubber base forming mold having a continuous sidewall, a floor and an open top. A hard positive impression is pressed into the soft stone material, excess overflow material is scraped away, and the soft stone material allowed to harden, adhering to the positive impression. The base and positive impression combine to form the dental cast, which has a uniform appearance due to the similar stone used in both the base and positive impression.

A variety of prior art methods for affixing dental casts made by pressing positive impressions into base forming molds to dental articulators are known. Young, U.S. Pat. No. 5,605,456, utilizes a cam clamp of the type used to secure automotive hoses. This hose clamp is wrapped around the base of the dental cast, and secured to a substantial dental articulator. Callne, U.S. Pat. No. 5,221,203, utilizes a wire loop that clips into brackets integral with the top of the base. The wire loop is attached to a screw wheel adjustable dental articulator. Both systems require articulators that are difficult to use and are expensive.

The Huffman patents utilize a variety of means to secure the dental base/cast to an articulator. Huffman utilizes a disposable single-use plastic articulator having hinged articulator arms with socket balls that snap into retention sockets mounted to the dental cast base. The retention sockets may be inserted into the still soft stone (Huffman '323), which requires the "proficiency and expertise of the technician" to decide when to insert the mounting such that proper alignment and securement is achieved. Other Huffman methods involve slots formed in the base by a shelf protruding into the interior cavity of the base forming mold. When the forming mold is removed (peeled off), slots and/or channels remain, into which a ridge tab is inserted and glued. The ridge tab has a socket that accepts a socket ball of the single-use articulator. When the upper and lower casts are aligned, a drop of quick drying glue is placed on the socket ball, and held until set. Some of the limitations of the Huffman devices are: 1) the difficulty in positioning the upper and lower casts while gluing their socket joints; 2) inability to make adjustments after gluing the socket joints; 3) inability to make adjustments/corrections to the lateral and vertical placement of the ridge tabs after gluing; 4) difficulty in storing dental casts due to space taken by the non-removable articulator; and 5) expense associated with not being able to reuse articulators on different casts.

Braun et al, U.S. Pat. No. 4,522,591 discloses an articulator for holding dental models. An upper mounting having a housing holds the upper jaw model and a lower mounting holds the lower jaw model and a cover is fastened to the housing of the upper mounting. The internal chamber of the housing holds a movable disk-shaped component which has a hinged socket extension that protrudes through a lower opening in the bottom of the housing and holds a ball to form a ball-and-socket joint. The ball has a threaded extension arm bolt that extends through an opening in the extension and has a mounting shoe fastened at the end thereof, which serves as the connection to the jaw model, which fits into the shoe. A shim is disposed in the internal chamber above the ball and has a concave contacting surface conforming to the surface of the ball. A threaded bolt extends through the cover above the shim and has a disk handle at its upper end. When the threaded bolt is turned, the front surface of the bolt pushes against the shim and presses it against the ball, causing the ball to be pressed against the internal wall of the extension and lock it into the desired position.

Cohn, U.S. Pat. No. 4,797,097 discloses a dental articulator for hingably retaining a pair of dental castings which comprises a pair of attachment members, each adapted to engage one of the castings and a hinge unit including two pivotally interconnected retaining members, each adapted to pivotally engage one of the attachment members by means of at least one ball and socket which may be selectively and reversably immobilized. The hinge unit further includes a hinge connection which provides a pair of pivot axes disposed in spaced apart parallel relationship, so that each retaining member is oriented to pivot about one of the axes; the hinge unit further provides for the reversible separation of the retaining members. In some embodiments, the ball portion of the joint is located on the retaining member and the socket on the attachment member, and in others, the ball is on the attachment member and the socket on the retaining member. The ball joint may be selectively or reversably immobilized by means of a locking screw threadedly mounted in the socket which engages the ball.

Farrell, U.S. Pat. No. 5,007,829 discloses a dental articulator having a posterior articulating assembly, an anterior incisal support assembly and a mold assembly. The posterior articulating assembly includes a ball and socket joint and a pivot joint. The ball and socket joint has a socket member which is operably coupled to the pivot joint and a ball member which is operably coupled to a first teeth cast. A set screw is threadedly mounted in the socket member to frictionally engage and lock the ball member at a desired position. The pivot joint has a pivot member operably coupled to a support member for joining the pivotal joint to a second teeth cast. The anterior incisal support assembly has an incisal pin operably joined to the first teeth cast and an incisal plate, which cooperates with the incisal pin, joined to the second teeth cast. The mold assembly has a plurality of molds each having an aperture in each of an anterior and posterior portion of the mold and an associated alignment protrusion, in close proximity to the aperture, for aligning joining members, to be cast into the first and second teeth casts, for connecting the first and second teeth casts to the ball member and the support member.

Pacino, Jr. et al, U.S. Pat. No. 6,508,646 discloses a securable mounting for an articulator for dental casts for receiving a ball portion of the articulator. The mounting comprises a rear wall, a bottom wall and laterally spaced side walls with extensions that form a partial cup or socket. A rectangular tongue connected to the rear wall is adapted to be inserted into a groove of the dental cast, and the ball portion of an articulator arm assembly is received in the partial cup or socket and secured by a screw engaged in the bottom wall of the mounting.

My previous U.S. Pat. No. 6,382,969, discloses a dental articulator system including a device and method of forming dental casts having a posterior clip. The posterior clip has a line of holes that receive male bulbous protrusions on the backside of a clip plate. A shaft extends outwardly from the front side of the clip plate and has a ball at its outer end which is received in a socket of at least one articulator arm to form an adjustable ball and socket joint. The adjustable ball and socket joint is secured in place with a hand tightenable screw threadedly engaged in the socket which applies force to the ball impinging it against the inner wall of the socket. The ball has dimples on its exterior surface that engage resistance nibs on the interior surface of the socket to lock the ball in place.

My published patent application 2008/0050694 discloses an improvement to the dental articulator of my U.S. Pat. No. 6,382,969, wherein reusable articulator arms are attached by adjustable ball and socket joints to the dental cast base during the base formation process. The adjustable ball and socket joints are secured in place with a hand tightenable screw which applies force through a plunger to the ball, impinging the ball against the inner wall of the socket of the ball and socket joint. Gross and fine horizontal alignment and vertical alignment are accomplished by adjusting the orientation of the articulator arm ball and socket joint. It does not require the use of glue, and the articulator arms can be re-used and interchanged between different sets of casts.

Callne, U.S. Pat. No. 7,112,061 discloses a dental articulator for connecting first and second dental models which includes upper and lower arms hingedly connected at their rear ends by a hinge. Each arm front end is connected by a coupling to a dental model. Each coupling includes a ball connected at lateral sides to the arm front end which has truncated front and rear sides, a central bore therethrough, and a concave rear socket having a central bore therethrough, a model connector having a neck with a concave end and an anchor at the opposed end extending from opposed sides of the neck. A threaded fastener extends through the central bore joining the model connector and rear socket to the ball such that the rear socket and model connector are movable rotationally, up and down, and side to side on the ball to a selected position. Each model connector is inserted into a rear bore of a mold such that the neck is disposed in the bore and the anchor is in the interior space of the mold and becomes cast into the model after a plaster, typically a pourable hardenable stone is poured into the interior space of the mold and hardens. Upper and lower dental models each include a holder of an incisor spacing assembly co-cast into the base which hold an incisor pin for adjusting the vertical spacing between the fronts of the dental models.

Some of the problems with the ball mounting arrangement of the Callne Patent, U.S. Pat. No. 7,112,061, are that it requires several small parts that can become lost or misplaced, it is difficult to assemble the rear socket and the model connector onto the ball, and the amount of rotational movement is limited by the difference in diameters between the outside diameter of the bolt and the inside diameter of the bore through the ball.

One of the problems associated with dental articulators having articulator arms that are attached to the dental cast by adjustable ball and socket joints in which the ball is secured in place with a set screw threadedly mounted onto the socket is that the set screws are very small and are prone to being accidentally dropped and easily lost. Another problem with small set screw members is that their tip end has a very small surface area relative to the surface of the ball, thus, it is difficult to apply sufficient force to effectively frictionally engage the ball against the inner wall of the socket to prevent slippage, and they are prone to cause galling of the ball surface.

One of the problems associated with dental articulators which provide a shim or plunger between the set screw and the ball is that the shim or plunger is small and difficult to install and remove and can be accidentally dropped and easily lost. Another problem with the dental articulators which provide a shim or plunger between the set screw and the ball is that the shim or plunger is typically unsupported and can drop into the socket cavity making it difficult to install and properly position the ball in the socket.

SUMMARY OF THE INVENTION

The present invention overcomes the aforementioned problems and is distinguished over the prior art in general, and these patents in particular, by a dental articulator system and method of forming dental casts which utilizes a dental articulator having upper and lower generally U-shaped articulator arms, each having a transverse portion with laterally spaced link members at each end. The laterally spaced link members of the upper and lower arms are pivotally connected together at one end and the transverse portion of each arm has a ball socket which receives a ball at the outer end of a respective model anchor, the opposed end of which is cast into a dental model. The model anchor ball is adjustably secured in the ball socket of the articulator arm transverse portion by a set screw coupled with a rotatable magnetic extension rod that are installed, removed, advanced, and retracted as a unit to facilitate fitting and positioning the ball in the socket, and allow relative rotation between the set screw and the extension rod when the extension rod is engaged on the ball, allow the ball to pivot about the longitudinal axis of the extension rod.

One of the significant features and advantages of the present invention is that the magnetically coupled set screw and rotatable extension rod allow relative rotation between the set screw and the rotatable extension rod while still connected, and when the extension rod engages the ball of the model anchor, rotation of the rotatable magnetic extension rod may stop while the set screw can be further rotated, thereby providing a firm ball engaging grip without marring the surface of the ball.

Another significant feature and advantage of the present invention is that the magnetically coupled set screw and rotatable extension rod allow relative rotation between the set screw and the rotatable extension rod thereby allowing the ball of the model anchor to pivot in the cavity of the ball socket about the longitudinal axis of the transverse portion of the articulator member.

Another significant feature and advantage of the present invention is that the magnetically coupled set screw and rotatable extension rod allow the set screw and the rotatable extension rod to be easily installed and removed as a unit, and to be advanced and retracted longitudinally in the transverse portion of the articulator member when the set screw is rotated, thereby allowing the ball of the model anchor to be snap fitted into the ball cavity of the socket portion and to be properly positioned in the socket without interference.

A further feature and advantage of the present invention is that the magnetically coupled set screw and rotatable extension rod allow the set screw and the rotatable extension rod can be handled and manipulated as a single unit and eliminate the need for manually installing and positioning separate small shims and plungers that can be accidentally be dropped and lost.

A still further feature and advantage of the present dental articulator is that it is simple in construction, inexpensive to manufacture, and rigged and reliable in operation.

Other features and advantages of the invention will become apparent from time to time throughout the specification and claims as hereinafter related.

BRIEF DESCRIPTION OF THE DRAWINGS

FIG. 1 is a perspective view of the dental articulator apparatus in accordance with the present invention, shown connected with a full arch forming mold.

FIG. 2 is an exploded perspective view of the dental articulator apparatus, shown from the end opposite that shown in FIG. 1, showing the articulator, model anchors, and a forming mold in an unassembled condition.

FIG. 3A is an exploded perspective view of the upper and lower articulator arms in an unassembled condition.

FIG. 3B is a front elevation view of the articulator and model anchors.

FIG. 3C is a side elevation view of the articulator arms and model anchors.

FIG. 3D is a top plan view of the articulator arms and model anchors.

DESCRIPTION OF THE PREFERRED EMBODIMENT

Figure 4:
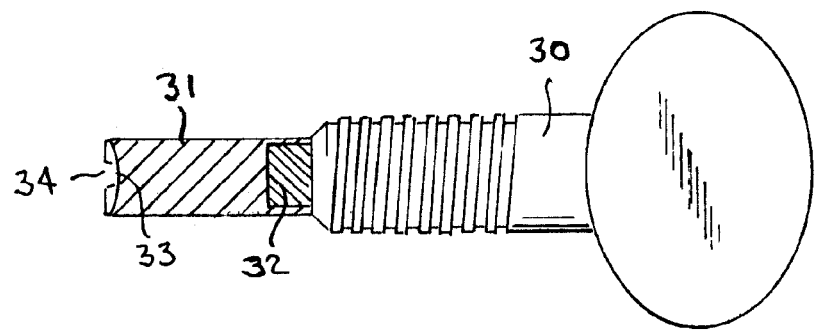
FIG. 4 is an enlarged side elevation view of the set screw and magnetically coupled rotatable magnetic extension rod member, with the magnetic extension rod shown in longitudinal cross section.

Referring to the drawings by numerals of reference, there is shown in FIGS. 1 and 2, an example of a preferred embodiment of a dental articulator apparatus 10, in accordance with the present invention. The dental articulator apparatus 10 includes an articulator 11 having an upper and a lower, generally U-shaped, articulator arm 12A and 12B, respectively, each integrally molded and having a generally cylindrical transverse portion 13 with a generally spherical ball socket 14 intermediate its opposed ends and flat laterally spaced link members 15A and 15B at each end of the transverse portion, the outer ends of which are pivotally connected together. The integrally molded link members 15A, 15B, extend from the ends of the transverse portion 13 along parallel spaced planes perpendicular to a longitudinal axis extending through the transverse portion. A model anchor 20 having a ball 21 at one end is rotatably received in the ball socket 14 of the transverse portion 13 of each articulator arm 12A, 12B. The model anchor 20 has a shank portion 22 extending outwardly from the ball 21 with a generally cup-shaped anchor portion 23 at the outer end thereof. As described in detail hereinafter, the cup-shaped anchor portions 23 of the model anchors 20 are received in a flexible upper forming mold 40 and lower forming mold 41, respectively, with the balls 21 extending outwardly therefrom. The model anchors 20 are preferably constructed of hard plastic or other suitable material of sufficient strength to support the components of the dental articulator.

Figure 7:
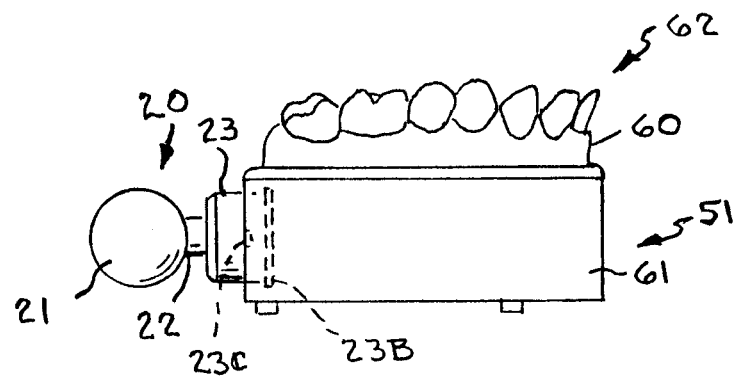
FIG. 7 is side elevation view showing the model anchor member embedded in a lower dental cast after the forming operation.
Figure 8:
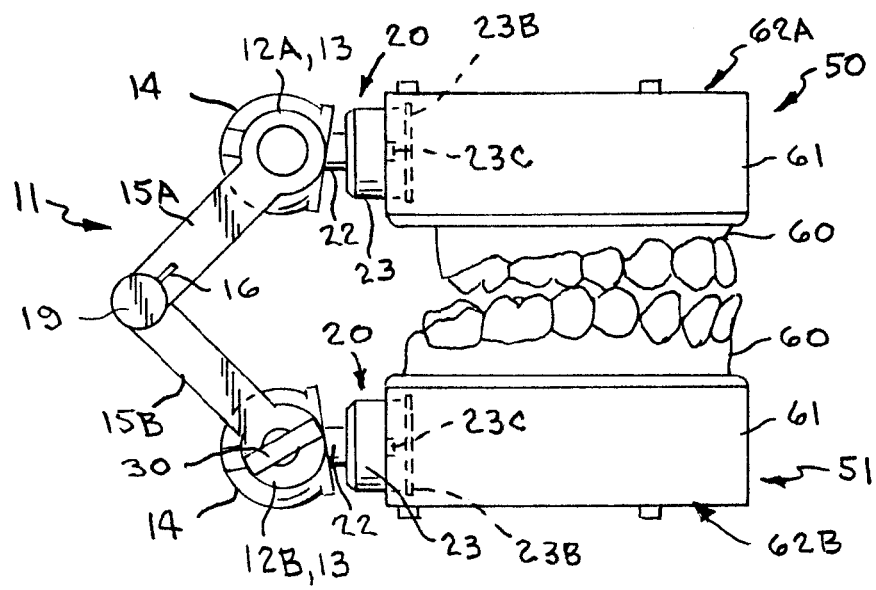
FIG. 8 is side elevation view showing the model anchor members embedded in a respective lower and upper dental casts with the balls of the model anchors mounted in the ball sockets of the articulator arms.

The flexible forming molds 40 and 41, also known as formers, are made of a flexible material such as rubber or silicone, and are used to make the dental casting models. Each forming mold 40, 41, has a base wall 42 surrounded by a generally U-shaped side wall 43 and an end wall 44 defining an interior cavity of sufficient volume to contain a quantity of casting stone upon which a positive impression can be pressed/bonded. The end wall 44 is provided with a central aperture 45 through which the ball 21 of a respective model anchor 55 extends. As shown in FIGS. 7 and 8 and described hereinafter, the upper forming mold 40 is for casting the upper (maxilla) dental casting model 50 and is similar, if not identical, to the lower forming mold 41 for the casting the lower (mandible) dental model 51.

Referring additionally to FIGS. 3A, 3B, 3C and 3D, the upper and lower articulator arms 12A and 12B will be described in greater detail. The upper and lower articulator arms 12A and 12B are of similar, if not identical construction. Each articulator arm 12A, 12B, has a generally cylindrical transverse portion 13 having a central generally spherical ball socket 14 and flat laterally spaced link members 15A and 15B at each end of the transverse portion, the outer ends of which are pivotally connected together. The outer end of laterally spaced link member 15A has a slot 16 extending inwardly from a beveled entrance opening 16A at its outer end. A hole 17 extends transversely through the slot 16 a short distance from the beveled entrance to form pair of opposed facing shoulders 16B. The outer end of laterally spaced link member 15B has an outwardly extending smaller diameter shaft 18 terminating in a larger diameter head 19. The diameter of the shaft 18 is smaller than the transverse hole 17. The laterally spaced link members 15A, 15B of the upper and lower articulator arms 12A and 12B are pivotally connected together by placing their outer ends in laterally opposed relation with the smaller diameter shafts 18 engaged on the beveled entrances 16A of the slots 16 and pressing the link members together such that the shafts pass over the inwardly facing shoulders 16B and snap fit into the transverse holes 17 to form the pivot connection.

Figure 5:
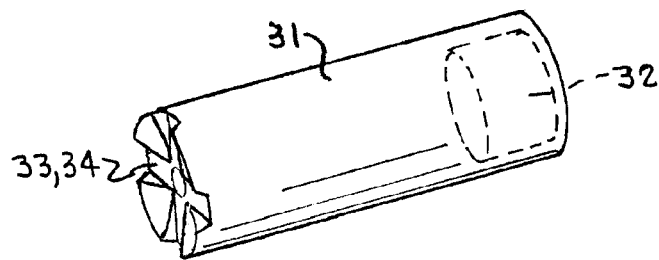
FIG. 5 is an enlarged perspective view of the rotatable magnetic extension rod member showing the concave surface and radial recesses on the ball engaging end.
Figure 6:
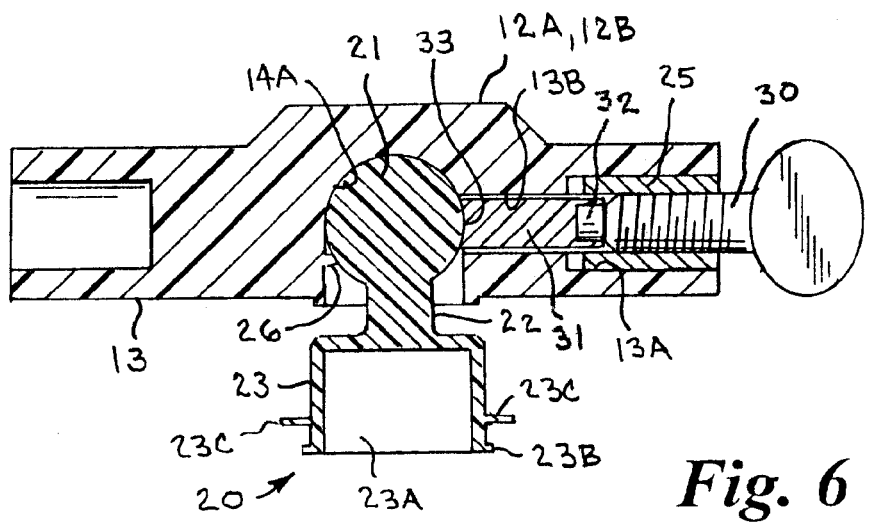
FIG. 6 is longitudinal cross sectional view through the transverse member of an articulator arm, taken along line 6-6 of FIG. 3B, showing the set screw and magnetically coupled rotatable magnetic extension rod member engaged on the ball of the model anchor.

Referring additionally to FIGS. 4, 5 and 6, the generally spherical ball socket 14 of each articulator arm 12A, 12B, has a generally semi-spherical interior cavity 14A which is open on one side for rotatably receiving the ball 21 at one end of the model anchor 20. One side of the transverse portion 13 of each articulator arm 12A, 12B has a larger diameter bore 13A extending inwardly from the outer end terminating in a smaller diameter bore 13B that extends into the semi-spherical interior cavity 14A of the ball socket 14. An internally threaded thread insert 25, typically metal, is secured in the larger diameter bore 13A by conventional means known in the art of plastic molding. Alternatively, the larger diameter bore 13A may be internally threaded. The semi-spherical interior cavity 14A of the ball socket 14 is provided with a raised lip 26 on the side opposite the smaller bore 13B over which the ball 21 of the model anchor 20 passes to snap fit into the interior cavity and thereafter be rotatably and releasably retained therein. A portion of the semi-spherical interior cavity 14A of the ball socket 14 opposite the smaller bore 13B may also be roughened.

FIG. 6 shows the model anchor 20 in greater detail. As described above, each model anchor 20 has shank portion 22 with a ball 21 at one end and a generally cup-shaped anchor portion 23 at the opposite end thereof. The model anchor 20 is preferably constructed of hard plastic or other suitable rigid material. The ball 21 may be provided with a rough surface finish. The cup-shaped anchor portion 23 has a recessed interior 23A and a raised lip 23B at the outer end. A pair of small rectangular protrusions or tabs 23C are disposed in diametrically opposed relation on the exterior of the cup-shaped anchor portion 23 and extend a short distance outwardly therefrom. The anchor portion 23 of the model anchor 20 may also be provided with additional anchoring means such as, for example, circumferentially spaced diverging wedge-shaped protrusions that extend axially from the outer end of the raised lip 23B.

The model anchor 20 is installed through a hole 45 in the end wall 44 of each upper and lower forming mold 40 and 41 such that the tabs 23C engage the interior facing surface of the end wall with a short portion the cup-shaped portion 23 disposed in the interior of the forming mold. A longer portion of the cup-shaped portion 23, the shank portion 22, and the ball 21 of the model anchor 20, extend a short distance outwardly from the end wall 44 of the respective forming mold 40, 41. When the casting stone is poured into the forming molds 40, 41, it flows into the recessed interior 23A and around the inward facing cup-shaped portion 23.

Referring again to FIG. 6 and additionally to FIGS. 4 and 5, a set screw 30 with a rotatable magnetic extension 31 magnetically coupled thereto are installed as a unit in the thread insert 25 in the transverse portion 13 of each articulator arm 12A, 12B such that the set screw is threadedly engaged in the thread insert and the magnetically coupled rotatable magnetic extension 31 extends into the smaller diameter bore 13B at one side of the semi-spherical interior cavity 14A of the ball socket 14.

The rotatable magnetic extension rod 31 is made of metal and has a recess 31A at one end and a permanent magnet 32 is secured in the recess. The opposite end 33 of the rotatable magnetic extension rod 31 is concave to correspond to the rounded circumference of the ball 21, and has a plurality of radial recesses 34. The recesses 34 in the concave end 33 reduce the surface area that is engaged on the surface of the ball 21. The set screw 30 is also metal and when the magnet 32 in the end of the rotatable magnetic extension rod 31 is engaged on the tip end of the set screw 30 they become coupled together due to the magnetic attraction. Thus, the set screw 30 with the magnetically coupled rotatable magnetic extension rod 31 can be easily installed and removed as a single unit, and can be advanced or retracted longitudinally in the transverse portion 13 of the articulator arm 12A, 12B, when the set screw is rotated in the thread insert 25 or backed out to allow the ball 21 of the model anchor 20 to be snap fitted into the cavity 14A of the ball socket 14 and to be properly positioned in the socket without interference.

After the ball 21 of the model anchor 20 is snapped into the ball socket 40, it is locked into position by tightening the set screw 30. Tightening the set screw 30 transmits force through rotatable magnetic extension rod 31 to the ball 21 of the model anchor 20, and impinges the ball 21 against the inner wall of the ball socket cavity 14A.

The set screw 30 with the magnetically coupled rotatable magnetic extension rod 31 allows relative rotation between the set screw and the rotatable extension rod while still connected. Thus, when the contoured surface at the end 33 of the rotatable magnetic extension rod 31 engages the surface of the ball 21, rotation of the rotatable magnetic extension rod 31 may stop while the set screw 30 continues to rotate, thereby preventing marring of the surface of the ball. This relative rotation also allows the ball 21 of the model anchor 20 to pivot in the cavity 14A of the ball socket 14 about the longitudinal axis of the transverse portion 13 of the articulator arm 12A, 12B. The magnetic extension rod 31 is impinged on the ball 21 and the ball is impinged in the socket cavity 14A when the set screw is tightened, thereby securing the ball within the socket 14 preventing the ball from rotating and preventing relative rotation between the magnetic extension rod and the set screw. The set screw 30 and rotatable extension rod 31 can be handled and manipulated as a single unit and eliminates the need for manually installing and positioning separate small shims and plungers that can be accidentally be dropped and lost.

OPERATION

Referring now to FIG. 2 and FIGS. 7 and 8, a model anchor 20 is installed through the aperture 45 in the end wall 44 of a respective flexible upper (maxilla) and lower (mandible) forming mold 40 and 41 such that the tabs 23C engage the interior facing surface of the end wall with a short portion the cup-shaped portion 23 disposed in the interior of the forming mold and a longer portion of the cup-shaped portion, the shank portion 22, and the ball 21 of the model anchor extend a short distance outwardly from the end wall 44 of the forming mold.

A pourable hardenable casting stone, also known as yellow stone, is poured into the flexible upper (maxilla) and lower (mandible) forming molds 40 and 41. When the casting stone is poured into the forming mold 40, 41, it flows into the recessed interior 23A and around the inward facing cup-shaped portion 23 of the model anchor 20. Optionally, a lubricant may be applied onto the interior surfaces of the forming molds 40 and 41 prior to inserting the model anchor 20 and pouring the casting stone to facilitate later peeling the molds away from the hardened casting stone.

The positive dental impression 60 is then pressed into the soft stone, and excess soft stone flowing over the top edge of the forming molds 40 and 41 is wiped or scraped away. The positive dental impression 60 is positioned in the forming molds 40 and 41 such that it protrudes away from the soft stone to emulate the patient's dental orientation, as is typical in the art. As the soft stone hardens forming the casting base 61, it binds to the positive dental impression 60, which together form the dental cast 62 (FIG. 7), and the cup-shaped portion 23 of the model anchor 20 becomes embedded in the casting base.

When the dental cast 62 has hardened, the forming molds 40 and 41 are pulled away from the casting base 61 for later re-use, leaving the dental cast 62 and the model anchor 20 embedded and attached thereto.

In the preferred embodiment, the dental articulator 11 is pre-assembled by snap fitting the articulator arms 12A, 12B, together such that they are pivotally connected, as described above. The balls 21 of the model anchors 20 are snapped into the ball socket 14 of the respective arms 40, 41, and the set screws 30 with the magnetically coupled rotatable magnetic extension rods 31 are left untightened.

The upper dental cast 62A and lower dental cast 62B are aligned to mechanically simulate axes of articulation, planes and arcs of occlusion, and lines, planes and axes of symmetry found in the patient's mouth. As seen in FIG. 8, the upper dental cast 62A and lower dental cast 62B are roughly aligned horizontally and vertically.

Fine vertical and horizontal alignment adjustments of the upper and lower dental casts 62A and 62B are made while the set screws 30 coupled with the magnetic extension rods 31 are still loose. When the alignment of the upper and lower dental casts 62A and 62B is proper, the set screws 30 coupled with the magnetic extension rods 31 are tightened down to engage the balls 21 of the model anchors 20, thereby impinging and securing the balls within the cavities 14A of the ball sockets 14. The impinged ball 21 in the socket prevents the ball from rotating which also prevents relative rotation between the magnetic extension rod 31 and the set screw 30. At this stage, the only free movement of the dental articulator 11 is the relative pivotal movement of the articulator arms 12A, 12B, about their pivotal connection. Thus, the upper dental cast 62A and lower dental cast 62B are free to pivot in simulation of the patient's natural jaw motion.

By backing the set screws 30 coupled with the magnetic extension rods 31 away from the balls 21, the model anchors 20 can be removed from the articulator arms 12A, 12B, and the dental casts 62A, 62B can be shipped and stored in a smaller volume, thus providing additional storage space and smaller shipping containers. The dental articulator 11 can easily be reattached to the dental casts 62A, 62B, and adjusted by the dentist, the dental technician or the laboratory technician. The same dental articulator 11 can be reused on any dental cast having the present model anchor 20.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A dental articulator apparatus comprising:
   an upper and a lower integrally molded generally U-shaped articulator arm, each having a transverse portion including oppositely disposed opposed ends with a laterally spaced link member extending from each of said oppositely disposed opposed ends, said laterally spaced link members of said upper and lower arms releasably and pivotally connected together at an outer end for relative pivotal movement, said transverse portion of each said arm having a ball socket intermediate said oppositely disposed opposed ends, and one of said oppositely disposed opposed ends having a threaded portion in communication with said ball socket;
   each said ball socket comprising a semi-spherical interior cavity having a raised lip disposed therein opposite said threaded portion is disposed in communication with said ball socket, each said ball socket is disposed between a corresponding one of said threaded portion and said raised lip, wherein a model anchor ball of a model anchor is passed over said raised lip to rotatably and releasably retain said model anchor ball at least partially within said semi-spherical interior cavity of said ball socket;
   a set screw magnetically coupled with a rotatable magnetic extension rod at a tip end of said set screw, said set screw threadedly engaged in said threaded portion of said transverse portion and said magnetically coupled rotatable magnetic extension rod having a first end disposed adjacent to said ball socket; and
   said set screw and said magnetically coupled rotatable magnetic extension rod being installed, advanced, and retracted in, and removable from said transverse portion as a unit.

2. The dental articulator apparatus according to claim 1, wherein said laterally spaced link members extend from said oppositely disposed opposed ends of said transverse portion along parallel spaced planes perpendicular to a longitudinal axis extending through said transverse portion.

3. The dental articulator apparatus according to claim 1, further comprising:
   said model anchor having said model anchor ball at one end and a generally cup-shaped anchor at a second end;
   said model anchor ball removably received and rotatably mounted in said ball socket of said transverse portion of a respective said articulator arm;
   said first end of said magnetically coupled rotatable magnetic extension rod disposed adjacent to said ball socket to be advanced into engagement with and disengaged from said model anchor ball upon rotation of said set screw;
   said set screw and magnetically coupled rotatable magnetic extension rod are advanced and retracted in said transverse portion as a unit and said extension rod rotates relative to said set screw when engaged on said model anchor ball to facilitate fitting and positioning said ball in said socket; and
   when said set screw is tightened, said coupled magnetic extension rod is impinged on said ball and said ball is impinged in said socket to secure said ball within said ball socket and prevent said ball from rotating and prevent relative rotation between said magnetic extension rod and said set screw.

4. The dental articulator apparatus according to claim 3, wherein said first end of said magnetically coupled rotatable magnetic extension rod has a concave surface disposed adjacent to said ball socket to be advanced into engagement with and disengaged from said model anchor ball upon rotation of said set screw.

5. The dental articulator apparatus according to claim 4, further comprising:
   a plurality of radial recesses in said concave surface of said outer end of said magnetically coupled rotatable magnetic extension rod for reducing the surface area that is engaged on said model anchor ball.

6. The dental articulator apparatus according to claim 3, further comprising:
   a flexible forming mold having a base wall surrounded by a contoured vertical peripheral wall and a contiguous end wall defining an interior space, and an aperture in said end wall;
   said generally cup-shaped anchor at said second end of said model anchor mounted through said aperture such that a portion of said cup-shaped anchor is disposed in said interior space of said forming mold, and said model anchor ball is disposed a short distance outwardly from said end wall.

7. The dental articulator apparatus according to claim 1, wherein a first one of said laterally spaced link members has a slot extending inwardly from a beveled entrance opening at an outer end and a hole extending transversely through said slot a short distance from said beveled entrance to form a pair of opposed facing shoulders;
   a second one of said laterally spaced link members has an outwardly extending smaller diameter shaft terminating in a larger diameter head at an outer end; and
   said laterally spaced link members of said upper and said lower articulator arm are pivotally connected together by placing said outer ends in laterally opposed relation with said smaller diameter shafts engaged on said beveled entrances and pressing said link members together such that said shafts pass over said inwardly facing shoulders and snap fit into said transverse holes to form a pivot connection.

* * * * *